United States Patent [19]
Schmitt

[11] Patent Number: 5,653,746
[45] Date of Patent: Aug. 5, 1997

[54] RADIALLY EXPANDABLE TUBULAR PROSTHESIS

[75] Inventor: Peter J. Schmitt, Garnerville, N.Y.

[73] Assignee: Meadox Medicals, Inc., Oakland, N.J.

[21] Appl. No.: 462,230

[22] Filed: Jun. 5, 1995

Related U.S. Application Data

[62] Division of Ser. No. 208,182, Mar. 8, 1994, Pat. No. 5,443,499.

[51] Int. Cl.$^6$ ..................................................... A61F 2/06
[52] U.S. Cl. ................................................. 623/1; 623/12
[58] Field of Search ................................. 623/1, 11, 12; 600/36; 606/195, 198, 194; 604/8

[56] References Cited

U.S. PATENT DOCUMENTS

| | | |
|---|---|---|
| 3,657,744 | 4/1972 | Ersek . |
| 4,776,337 | 10/1988 | Palmaz . |
| 4,792,336 | 12/1988 | Hlavacek et al. . |
| 4,834,755 | 5/1989 | Silvestrini et al. . |
| 4,877,030 | 10/1989 | Beck et al. . |
| 4,922,905 | 5/1990 | Strecker . |
| 5,061,275 | 10/1991 | Wallstén et al. . |
| 5,078,726 | 1/1992 | Kreamer . |
| 5,123,917 | 6/1992 | Lee . |
| 5,211,658 | 5/1993 | Clouse . |
| 5,236,447 | 8/1993 | Kubo et al. . |
| 5,275,622 | 1/1994 | Lazarus et al. . |
| 5,306,294 | 4/1994 | Winston et al. . |
| 5,316,023 | 5/1994 | Palmaz et al. . |
| 5,330,500 | 7/1994 | Song . |
| 5,354,310 | 10/1994 | Garnic et al. . |
| 5,356,423 | 10/1994 | Tihon et al. . |
| 5,360,443 | 11/1994 | Barone et al. . |
| 5,366,504 | 11/1994 | Andersen et al. . |
| 5,376,376 | 12/1994 | Li . |
| 5,383,926 | 1/1995 | Lock et al. . |
| 5,387,235 | 2/1995 | Chuter . |
| 5,405,378 | 4/1995 | Strecker . |
| 5,405,379 | 4/1995 | Lane . |
| 5,425,765 | 6/1995 | Tiefenbrun et al. . |

FOREIGN PATENT DOCUMENTS

| | | |
|---|---|---|
| 0 183 372 | 6/1986 | European Pat. Off. . |
| 0 292 587 | 11/1988 | European Pat. Off. . |
| WO 90/04982 | 5/1990 | WIPO . |

OTHER PUBLICATIONS

Textile Progress, *Vascular Grafts: Textile Structures and Their Performance.* B. Pourdeyhimi, Ph.D., C. Text., A.T.I., vol. 15, No. 3, pp. 1–30 (1986).

*Primary Examiner*—Debra S. Brittingham
*Attorney, Agent, or Firm*—Hoffmann & Baron

[57] ABSTRACT

A radially expandable tubular prosthesis which allows for controlled expansion in a circumferential direction following implantation while limiting expansion in a longitudinal direction. The prosthesis is particularly suited to intraluminal implantation via a catheter and is also particularly suited for percutaneous implantation in children.

10 Claims, 5 Drawing Sheets

RADIALLY EXPANDABLE TUBULAR PROSTHESIS

This is a divisional of application(s) Ser. No. 08/208,182 filed on Mar. 8, 1994, now U.S. Pat. No. 5,443,499.

BACKGROUND OF THE INVENTION

The present invention relates to a tubular prosthesis and, more particularly, to a radially expandable tubular prosthesis which allows controlled expansion in a circumferential direction following implantation while limiting expansion in a longitudinal direction.

The typical prosthesis of the prior art is manufactured with a predetermined diameter, that is, prostheses are manufactured in various sizes so that the physician may choose the most appropriate-sized prosthesis to replace or repair the damaged lumen in the patient. As far as length is concerned, the physician merely cuts the chosen prosthesis to size, the prosthesis typically being oversized in the longitudinal direction.

The commonly-employed prosthesis mentioned above is suitable for use in many situations. However, several applications may demand that the prosthesis be expandable in the radial direction. For example, one such application involves intraluminal implant procedures in which the prosthesis is delivered to a damaged lumen via a catheter. The technique requires that the implant be stored within the catheter (e.g., it may be rolled or bunched) prior to insertion of the catheter into the patient. Upon advancement of the catheter to the site of the damage, the implant is expelled from the catheter, unrolled (or unfolded) and thereafter secured to the lumen. Because of the procedure, it is difficult, if not impossible, for the physician to correct any mismatch in sizing that may occur between the implant and the host lumen. For example, if the physician miscalculates the size of the lumen receiving the implant or should the lumen prove to be larger or smaller than anticipated by the physician, the physician may not be able to securely fix the implant to the host lumen.

Another application in which it would be desirable to employ an expandable prosthesis involves the area of pediatrics. A common disadvantage encountered in conventional pediatric prostheses is the inability of the device to accommodate growth changes in the surrounding tissue as the child ages. Consequently, it is often necessary to perform several surgical procedures on a child to implant ever increasingly circumferentially-larger prostheses. It has traditionally been necessary to entirely remove and replace the implanted prosthesis with a larger-sized prosthesis as the child grows. Such a series of surgeries is traumatic to the body and has a degree of risk inherently associated therewith.

Accordingly, it would be desirable to provide a tubular prosthesis which allows for circumferential expansion such that the prosthesis could be readily deployed via a catheter for intraluminal delivery and, further, such that the prosthesis could be circumferentially expanded in vivo as the child grows, thereby eliminating the need, or at least the frequency, for surgical replacement of the implant.

SUMMARY OF THE INVENTION

The present invention, which addresses the needs of the prior art, provides a radially expandable tubular prosthesis. Any type of textile pattern may be used in manufacturing the prosthesis provided its structure will allow for use of undrawn or partially drawn yarns which will provide circumferential expansion, the primary purpose being the ability to be drawn in vivo subsequent to implantation, e.g., via balloon catheter or the like. For example, woven, knitted, braided and filament wound fabrics may be used. Thus, in one embodiment, the prosthesis is made from a polymeric fabric having a sufficient portion of yarn which is capable of being drawn beyond the yield point of plastic deformation upon the application of force thereto sufficient to exceed the yield point to allow for radial expansion of the prosthesis.

The prosthesis of the present invention may be used in a wide variety of applications. For example, the prosthesis may be employed as a graft in the vascular system, as well as the esophageal, stomach and bowel areas. Alternatively, the prosthesis may be intraluminally implanted via a catheter or similar device to repair or support a weakened or damaged lumen, such as a blood vessel in the vascular system.

In one preferred embodiment, the prosthesis is made from a woven fabric having substantially drawn longitudinal yarns (warp yarns) which limit expansion or elongation of the prosthesis in the longitudinal direction, and radial yarns (fill yarns) which are at most partially drawn to allow for expansion of the prosthesis in the radial direction when the yield point of he radial yarns is exceeded.

The present invention also provides a method for intraluminally repairing a damaged lumen with an expandable prosthesis via a catheter. The method includes the step of introducing the catheter intraluminally to the damaged lumen. The method also includes the step of delivering the prosthesis intraluminally at the site of damage in the lumen. The method includes the further step of expanding the prosthesis circumferentially until its diameter substantially conforms to that of the damaged lumen.

Due to its unique features, delivery of prostheses to damaged vessels can be accomplished using less invasive methods than conventional implant surgery and with more ease and less uncertainty than conventional methods requiring coiling or folding of the device during delivery via a catheter. The prostheses of the present invention can be delivered intraluminally via a catheter without the need for conventional bunching, folding or rolling of the prosthesis for stowage in the catheter. Instead, the catheter is initially formed with a sufficiently small diameter that allows the prosthesis to be stowed on the catheter without rolling or bunching, delivered to the site of deployment, expanded to the proper size and deployed. Because the prosthesis is not rolled or bunched, the delivery process is more readily accomplished and, in addition, the prosthesis may be more easily maneuvered inside the lumen. (However, depending upon the degree of expandability, the graft may still need to be bunched or rolled, but to a lesser degree than a non-expandable graft.) Further, the prosthesis of the present invention may be implanted in a child, and, thereafter, expanded via a balloon catheter to enlarge the diameter of the implanted prosthesis to substantially conform with the enlarged diameter (due to growth) of the host lumen.

The present invention also provides a method for reducing the frequency of surgical replacement of a previously implanted prosthesis in a child. The method includes the step of implanting an expandable prosthesis in a child. The method includes the additional step of delivering internal force to the prosthesis following a period of growth in the child sufficient to expand the prosthesis in a circumferential direction until the diameter of the prosthesis substantially conforms to that of a connecting host lumen which has experienced a period of circumferential growth following a period of growth in the child. The method includes the further step of expanding the prosthesis in a circumferential direction until the diameter of the prosthesis substantially conforms to the diameter of a connecting host blood vessel which has experienced a period of circumferential growth.

It is apparent from the above discussion that the present invention overcomes important disadvantages of the prior art and satisfies a strong need in the medical industry.

DETAILED DESCRIPTION OF THE INVENTION

Figure 1:
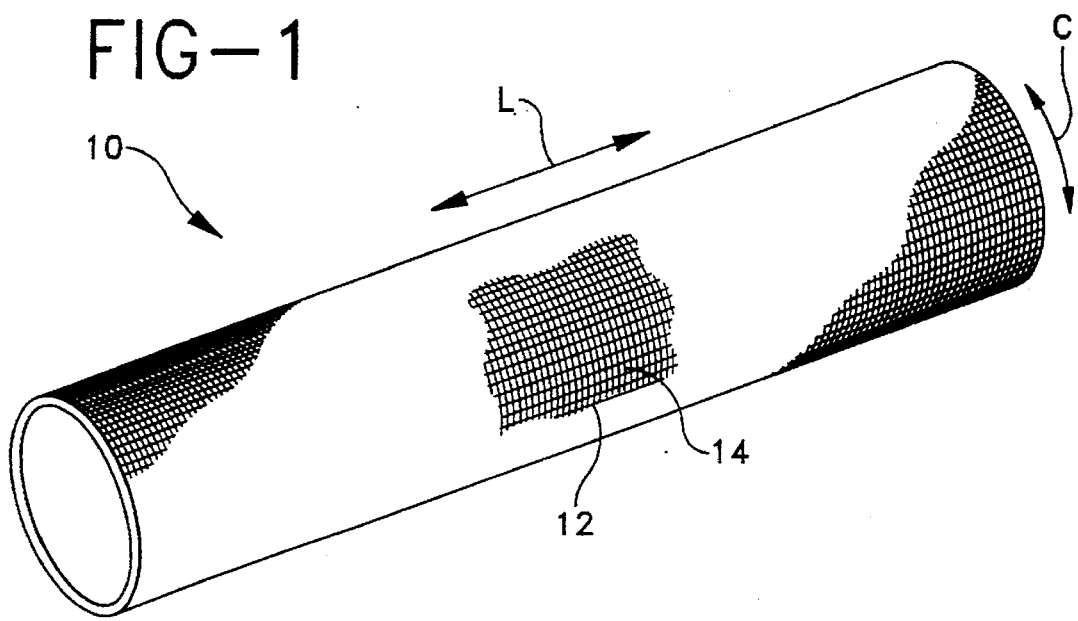
FIG. 1 is a perspective view of a woven tubular prosthesis.
Figure 2:
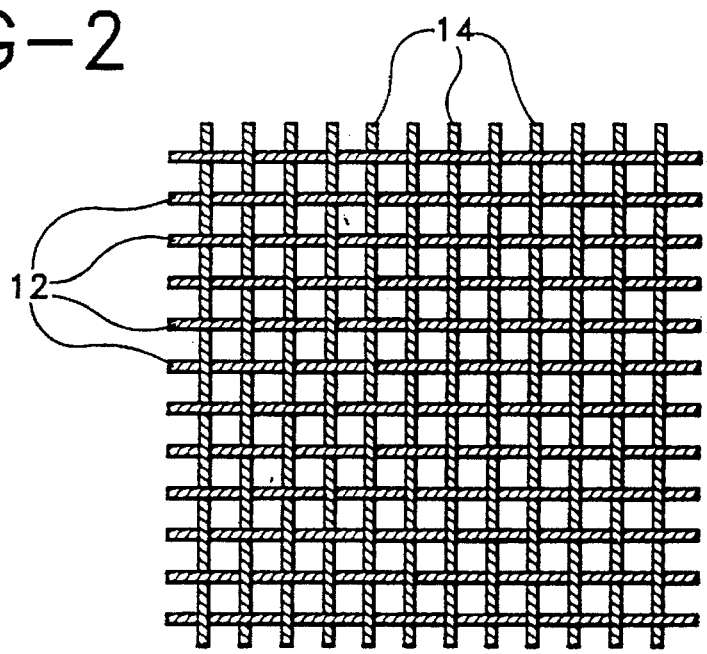
FIG. 2 is a schematic of a traditional weave pattern.

Referring to the drawings and, in particular to FIGS. 1–2, a woven tubular prosthesis 10 is shown. The weave pattern includes warp yarns 12 running along the longitudinal length L of the woven product and fill yarns 14 running around the circumference C of the product.

As is well-known to those skilled in the art, the yarns used in a woven product are typically treated and processed prior to weaving. This treatment commonly includes the step of "drawing" the yarns, i.e., longitudinally stretching the yarns beyond their yield point until complete plastic deformation is accomplished.

Figure 3:
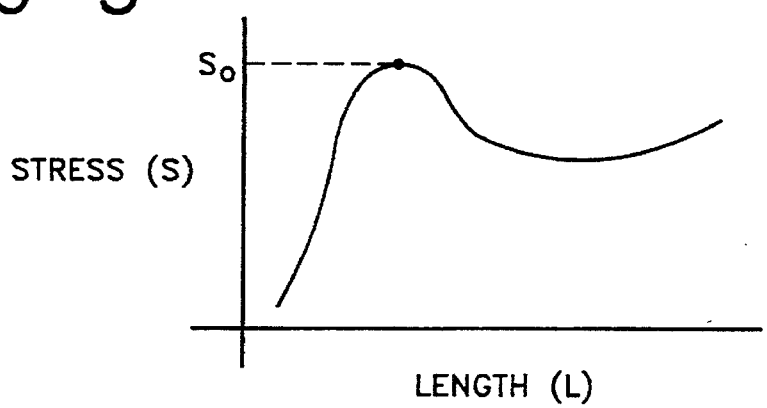
FIG. 3 is a graph illustrating the stress vs. length relationship for a typical synthetic yarn having been drawn through the yield point of plastic deformation ($S_o$)

Referring to FIG. 3, the force required to "draw" a yarn increases until the yield point is reached, at which point, the yarn enters a region of plastic deformation (i.e., a region in which the yarn now exhibits loss of its elasticity and ability to change appreciably in length). Once the deformation point in a yarn has been reached through stretching, the material has substantially lost its elastic memory and is more or less "fixed," neither being able to be further stretched or to return to its original length. Yarns which have experienced full deformation through the drawing process are typically used in prostheses because they are ideal for maintaining constant pressures without concern for undesirable stretching or bulging during use. Consequently, these prostheses are by necessity of fixed diameter.

As mentioned above, the present invention utilizes yarns, in the circumferential direction of the tubular prostheses, which have not been drawn or only partially drawn, allowing for future radial expansion through in vivo drawing, i.e., stretching, beyond the yield point, at which time the tubular prosthesis remains fixed at the increased diameter. This type of stretching causes the yarn to undergo inelastic strain, commonly referred to as plastic deformation, whereby the polymer molecules become newly aligned. The yarn may also be stretched until a point at which the material fractures (the fracture point). The process of drawing the yarn (to a point prior to the fracture point), increases the tensile strength of the yarn and decreases the elongation to failure.

With respect to prior art prosthesis, both of these characteristics (namely, increased tensile strength and decreased elongation) are desirable in that the prior art devices are typically produced to precise diameters in order to approximately match the size of the damaged lumen being repaired. However, several situations exist in which it would be desirable to be able to implant a prosthesis of a relatively small diameter and, thereafter, expand the prosthesis while such prosthesis remains positioned in the patient's body.

As mentioned above, the first application of what may be referred to as an expandable prosthesis concerns intraluminal implantation. In this application, the present invention functions as an endoprosthetic device, i.e., it is employed to internally repair or support a weakened or damaged lumen, e.g., a blood vessel in the vascular system. More particularly, a tubular prosthesis may be implanted in the body by delivering such prosthesis to the damaged lumen via a catheter. Delivering the prosthesis in such a manner greatly reduces the invasiveness of the procedure. For example, assuming a blood vessel positioned in the thorax is damaged, the typical prior art technique would require opening of the chest and rib cage to allow access to the damaged vessel. In contrast, intraluminal implantation eliminates the need, in many situations, for the surgeon to perform highly invasive procedures on the patient. Instead of accessing the lumen at the point of damage, the physician accesses a lumen leading to the damaged site, e.g., the femoral artery in the groin region when an artery in the vascular system requires repair.

Presently, the prostheses being intraluminally implanted are substantially the same prostheses that are implanted invasively. It has been discovered however, that if a prosthesis is woven with undrawn or partially drawn radial yarns, the prosthesis will be capable of circumferential expansion following manufacture of the product. More particularly, if a balloon catheter (or similar device) is inserted into such a prosthesis and is thereafter expanded, the prosthesis will circumferentially expand a slight degree until the yield point is reached. At that point, the radial yarns, i.e., fill yarns, which were not drawn, will plasticly deform, thereby allowing substantial circumferential expansion. The fill yarns, once expanded, will retain their expanded circumferential length. In addition, as mentioned above, the expanded yarns will generally exhibit a greater tensile strength than before.

To secure the prosthesis to the host lumen, a stent may be incorporated into the prosthesis. In that way, both the prosthesis and the stent can be simultaneously and controllably expanded to the desired diameter or until the prosthesis substantially conforms to the diameter of the host lumen. Any suitable means of attaching the stent to the expandable prosthesis, such as hooks, catches, sutures or other similar means may be used. Additionally, the stent may include similar means capable of anchoring the prosthesis in place in the host lumen.

Figure 4:
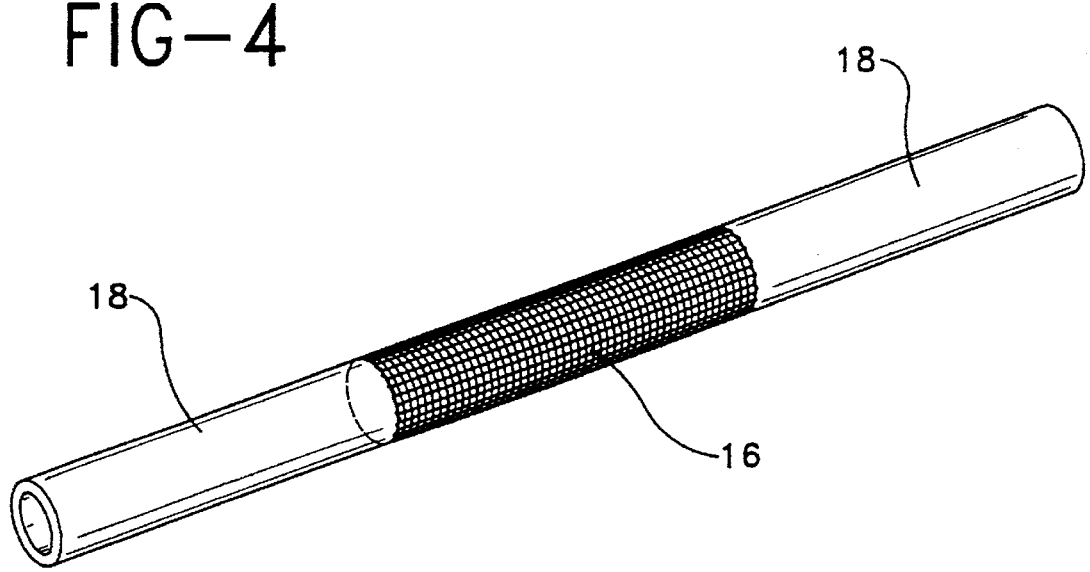
FIG. 4 is an illustration of an implanted tubular prosthesis.

As also mentioned above, the expandable prostheses of the present invention can be used as pediatric implants. More particularly, implanting prostheses in children can prove quite challenging because as children grow, the lumens, e.g., blood vessels, in their bodies also grow (both longitudinally and circumferentially). FIG. 4 illustrates an implant 16 in a blood vessel 18 of a child. At the time of implantation, the vessel is matched to the site of the connecting host vessels. However, as the child grows, the host vessels grow circumferentially, while the implant remains the same size.

Figure 5:
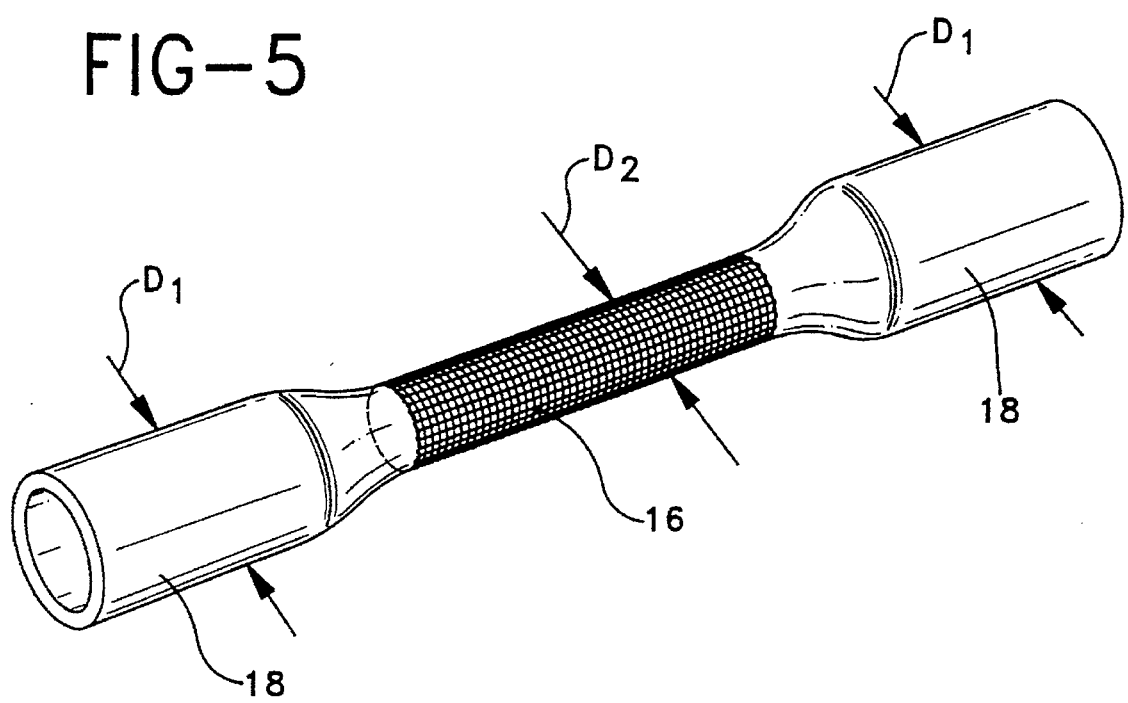
FIG. 5 is an illustration similar to FIG. 4 following a period of growth in the host lumen.
Figure 6:
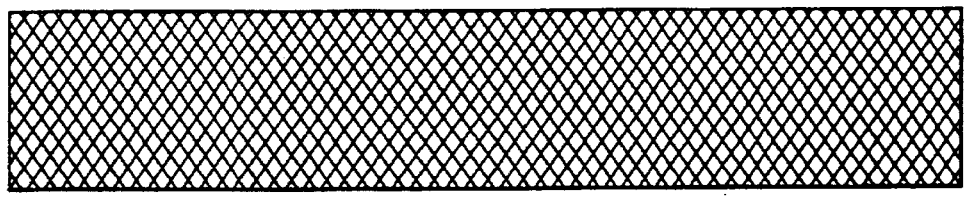
FIG. 6 is a perspective view of a braided tubular prosthesis.
Figure 6A:
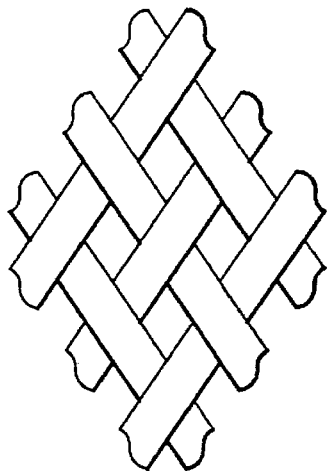
FIG. 6a is a schematic of a diamond braid.
Figure 6B:
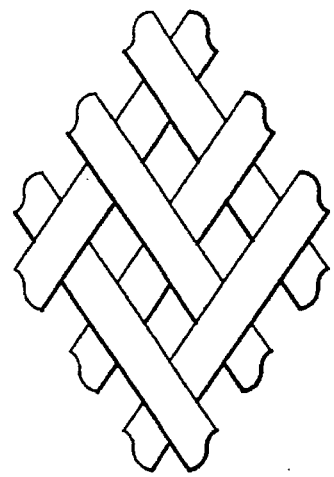
FIG. 6b is a schematic of a regular braid.
Figure 6C:
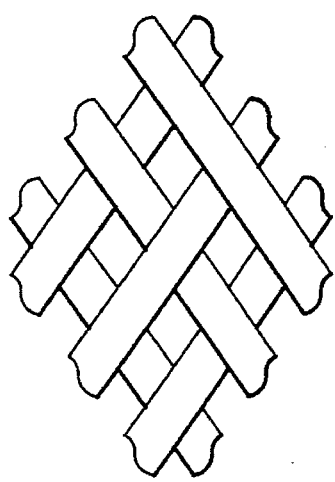
FIG. 6c is a schematic of a hercules braid.

Referring to FIG. 5, this period of growth in the child results in the formation of a "bottleneck" effect in the blood vessel. In other words, the blood must pass from a vessel having a diameter $D_1$, to a vessel having a reduced diameter $D_2$ and then to a vessel again having a diameter $D_1$. This obstruction in the vessel creates a stenosis, which, in turn, reduces blood flow to distal vessels. Further, increased pressure at the junction of the host vessel and graft can be problematic, if not fatal. Insufficient blood supply distal to the stenosis can also cause fatigue and diminished activity levels.

To reduce the risks associated with this phenomenon, physicians routinely remove and replace vascular grafts that have been implanted in children. In turn, a larger-sized graft is implanted in the child, which after a period of growth, will itself have to be removed and replaced. Overall, it may be necessary to perform a large number of surgical procedures on a child requiring a vascular graft, particularly if the child is an infant (during which time rapid growth occurs). As may well be imagined, performing frequent surgical procedures on a child can severely weaken the child, both physically and psychologically.

The expandable prosthesis of the present invention therefore provides a means for reducing (or eliminating) the frequency at which surgical replacement of an implanted graft is necessary. More particularly, an expandable prosthesis is first surgically implanted in a child. After a period of growth in the child, a procedure is performed whereby internal force is delivered to the prosthesis sufficient to expand the prosthesis in a circumferential direction until the diameter of the prosthesis substantially conforms to that of a connecting host lumen which has experienced a period of circumferential growth. This procedure may be accomplished by, for example, a catheterization procedure whereby a balloon catheter is advanced to the site of the graft. The balloon catheter is thereafter inflated until the yield point of the radial fill yarns is exceeded and the graft begins to expand. The graft may then be circumferentially expanded until its diameter is made substantially equivalent to the diameter of the host vessel.

In both of the describe applications, sufficient undrawn or partially drawn yarns must be present in the circumferential direction such that the yield strength would be well in excess of physiological pressure. Thus, the chosen yarn must be sufficiently strong in the radial direction of the graft in the undrawn state to resist harmful fluxuations in diameter or bulging in the unexpanded state. A minimum pressure ratio of about 10:1 yield strength to physiological pressure would suffice. For example, physiologic pressure for hypertensive patients is typically in the 2–4 psi range. This means that the hoop yield strength of the prosthesis should preferably be at least 40 psi to ensure no occurrence of premature expansion. Thus, to induce expansion of the prosthesis, a pressure of at least 40 psi would be required to be introduced. As mentioned above, while it is preferred that expansion be accomplished by balloon catheter, other means suitable to the application may be used.

Figure 7:
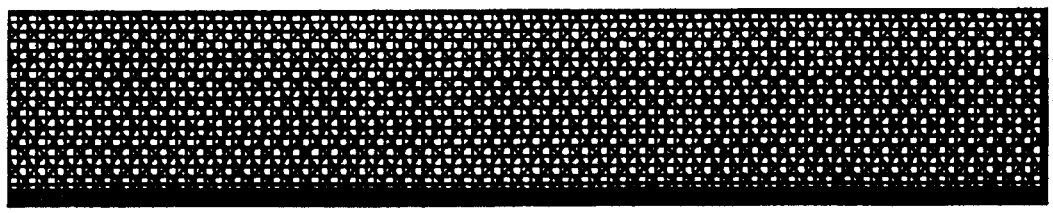
FIG. 7 is a perspective view of a knitted tubular prosthesis.
Figure 7A:
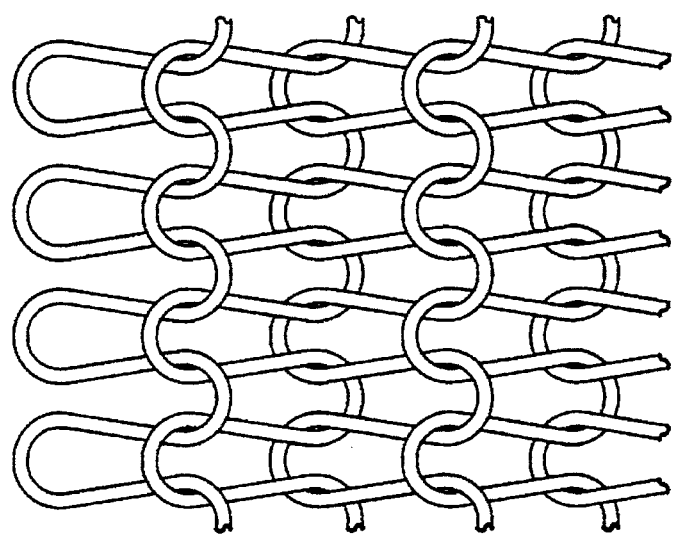
FIG. 7a is an enlarged detail of FIG. 7.
Figure 8:
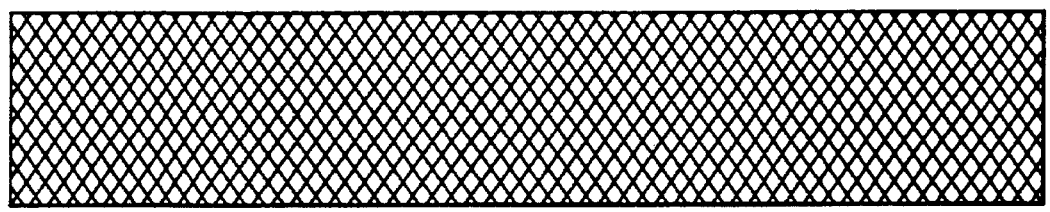
FIG. 8 is a perspective view of a filament wound tubular prosthesis.
Figure 8A:
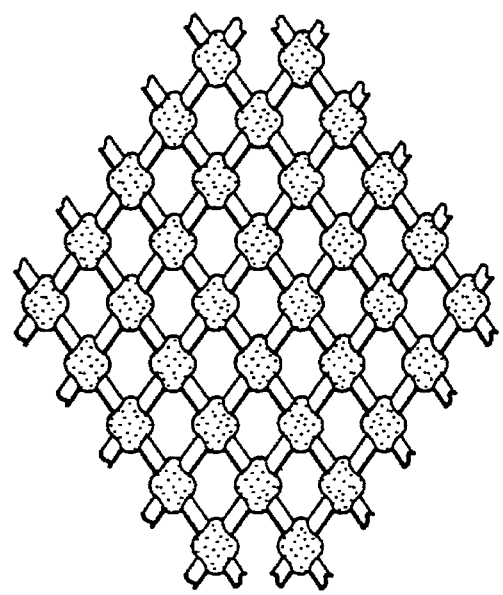
FIG. 8a is an enlarged detail of FIG. 8.

Although the above discussion has been directed to weaves (i.e., woven products), the same result can be accomplished with braided prosthesis (see FIGS. 6 and 6a–6c), knitted grafts (see FIGS. 7 and 7a) and filament wound prosthesis (see FIGS. 8 and 8a). As further discussed in the following examples, each of these prostheses can be manufactured to allow circumferential expansion following implantation.

The yarns in the present invention may be selected from a wide variety of synthetic polymers. Among the useful classes of materials are polyesters, polypropylene, polyurethane, polyamide, and copolymers thereof. Those yarns which are chosen for the undrawn, expandable portion of the prosthesis must be capable of withstanding physiological pressures in the undrawn state. In essence, these yarns must in the undrawn state resist any appreciable expansion or distortion under conditions of pressure and stress encountered in the body until such time as expansion is necessary. Expansion pressures will vary depending for the most part on the physical characteristics of the chosen material, but will by necessity exceed the yield point to reach the plastic deformation state at which time the material will remain in the expanded state. As previously stated, for safety reasons, the yield point of the material should preferably exceed the inherent physiological pressures of the host lumen by a factor of at least about ten. Thus, the force required to expand the circumference of the prosthesis is sufficiently high to resist change and remain in the undrawn state until manually expanded via catheter or similar device.

In the manufacture of the prostheses of the present invention, both drawn yarns as well as undrawn or partially drawn yarns are employed. The undrawn or partially drawn yarns are incorporated into the chosen textile pattern in the direction which upon drawing will result in a larger diameter of the device. In the case of woven patterns, the undrawn materials make up the fill yarns. In the case of knitted construction, such as weft knits, or braided patterns such as two dimensional, multiply or three dimensional braids, the undrawn yarns may comprise part of or all of the fabric. The same applies to grafts made from filament winding construction.

As a result of drawing, the polymeric yarns become directionally aligned or oriented. Drawing is generally accomplished at elevated temperatures, although alternatively cold drawing at high speeds is possible. As the polymer cools and recrystallizes, the elongated molecular chains become arranged in a new order which gives a higher modulus and increased stiffness to the yarn. The result is a loss of elongation with a higher strength:strain ratio.

EXAMPLES

Example 1

Woven Construction

The following specifications are used to fabricate a woven prosthesis of the present invention.
Weave—1/1 Plain, Tubular
Warp Yarn—Textured 50 denier/48 filaments polyester fully oriented (drawn)
Fill Yarn—Flat 115 denier/100 filament partially oriented (partially drawn) polyester
Ends per inch—160
Picks per inch—120

Subsequent to weaving the prosthesis, the fabric is scoured in a basic solution of warm water (e.g., 120° F.) and detergent, followed by rinsing to remove the detergent. The prosthesis can then be attached to a stent fixation device and assembled into a catheter delivery system, or, alternatively surgically implanted. Thus the expandable prosthesis can then be delivered intraluminally or be implanted percutaneously.

The partially-oriented fill yarn chosen in this example has the ability to stretch about 1.7 times its original length. Thus, if the woven graft were manufactured to a diameter of 10 mm, dilation with a balloon catheter to about 17 mm can be achieved.

Example 2

Braided Construction

The following specifications are used to fabricate a braided prosthesis of the present invention:
Braid—Regular Twill Braid, Tubular
Yarn—2 ply/flat 115 denier/100 filament partially oriented (partially drawn) polyester
Carriers—96
Helix Angle—55°
Diameter—10 mm Subsequent to braiding of the prosthesis (see FIGS. 6 and 6a–6c), the fabric is scoured in a basic solution of warm water (e.g., 120° F.) and detergent, followed by rinsing to remove the detergent. The prosthesis can then be attached to a stent fixation device and assembled into a catheter delivery system or, alternatively surgically implanted. Thus, the expandable prosthesis can then be intraluminally delivered or implanted percutaneously.

The partially-oriented fill yarn chosen in this example also has the ability to stretch about 1.7 times its original length. Thus, a braided prosthesis manufactured to a diameter of 10 mm would be capable of expanding to about 17 mm in diameter.

Example 3

Weft Knitted Construction

The following specifications are used to fabricate a knitted prosthesis of the present invention:
Knit—Tubular Jersey Weft Knit
Yarn—3 ply/flat 115 denier/100 filament partially oriented (partially drawn) polyester
Wales per inch—30
Courses per inch—40

After knitting (see FIGS. 7 and 7a), the fabric is scoured in a basic solution of warm water (e.g., 120° F.) and detergent. It would be rinsed to remove the cleaning agents. The prosthesis can then be attached to a stent fixation device and assembled into a catheter delivery system for insertion into the body or, alternatively directly implanted.

The partially-oriented fill yarn has the ability to stretch about 1.7 times its original length. The knitted fabric geometry provides an additional amount of stretch of about 50% to the overall dilation of the graft. Knitted prostheses manufactured to a diameter of about 10 mm are capable of being dilated with a balloon catheter to about 22 mm.

A warp knit construction can also be used. For example, instead of a tubular jersey weft knit construction, a tubular double tricot warp knit construction with similar stitch density can be used.

Example 4

Filament Wound Construction

A one ply/flat 115 denier/100 filament partially oriented polyester yarn is filament wound onto a mandrel of known diameter. The helix angle achieved is about 55°. The mandrel is wrapped with the yarn in both directions to provide biaxial reinforcement. To hold the yarns in place, they are passed through a solution of solvated polyurethane elastomer, such as Biomer® solution, sold by Johnson & Johnson. The solvent is removed, causing the polyurethane to dry and glue the yarns together. After filament winding (see FIGS. 8 and 8a), the material is scoured in a basic solution of warm water (e.g., 120° F.) and detergent, followed by rinsing to remove the detergent. The prosthesis can then be attached to a stent fixation device and assembled into a catheter delivery system for delivery intraluminally or, directly implanted.

In all four examples, the prosthesis may be of a straight, bifurcated or otherwise designed configuration.

Thus, while there have been described what are presently believed to be the preferred embodiments of the invention, those skilled in the art will realize that various changes and modifications may be made to the invention without departing from the spirit of the invention, and it is intended to claim all such changes and modifications which fall within the scope of the invention.

What is claimed is:

1. A method for intraluminally repairing a damaged lumen in a patient comprising:

delivering an expandable prosthesis to a site of damage in said lumen, said prosthesis being formed from a tubular substantially fluid-impermeable polymeric fabric having yarns which extend around the circumference of said fabric and which are sufficiently undrawn to allow for controlled inelastic radial expansion upon the application of a preselected radial force thereto; and delivering an internal preselected radial force to said prosthesis sufficient to inelastically expand said prosthesis.

2. The method of claim 1, wherein said prosthesis is expanded via a balloon catheter.

3. The method of claim 1, wherein said prosthesis includes means for securing said prosthesis to said lumen.

4. The method of claim 3, further comprising the step of securing said expandable prosthesis to said lumen.

5. The method of claim 1, wherein said lumen is a blood vessel.

6. The method according to claim 1, wherein said prosthesis is delivered intraluminally to said damaged lumen via a catheter.

7. The method of claim 6, wherein said prosthesis is initially sized for intraluminal delivery via said catheter without need for rolling or bunching of said prosthesis.

8. The method according to claim 6, wherein said prosthesis is expanded until its diameter substantially conforms to that of said damaged lumen.

9. The method according to claim 1, wherein said patient is a child, and said prosthesis is surgically implanted in said child.

10. The method according to claim 9, wherein said prosthesis is expanded following a period of growth in said child until its diameter substantially conforms to that of a connecting host lumen which has experienced a period of circumferential growth.

* * * * *

UNITED STATES PATENT AND TRADEMARK OFFICE
CERTIFICATE OF CORRECTION

PATENT NO. : 5,653,746
DATED : August 5, 1997
INVENTOR(S) : Schmitt

It is certified that error appears in the above-indentified patent and that said Letters Patent is hereby corrected as shown below:

At column 8, lines 28-29, delete "having yams which" and insert therefor --having yarns which--.

Signed and Sealed this

Fourteenth Day of October, 1997

*Attest:*

BRUCE LEHMAN

*Attesting Officer*  *Commissioner of Patents and Trademarks*